United States Patent [19]

Riester

[11] 4,416,287
[45] Nov. 22, 1983

[54] DISCHARGE VALVE FOR A BLOOD PRESSURE MEASURING DEVICE OR THE LIKE

[75] Inventor: Karlheinz Riester, Jungingen, Fed. Rep. of Germany

[73] Assignee: Rudolf Riester GmbH & Co., KG, Jungingen, Fed. Rep. of Germany

[21] Appl. No.: 308,540
[22] PCT Filed: Jan. 27, 1981
[86] PCT No.: PCT/EP81/00010
§ 371 Date: Sep. 28, 1981
§ 102(e) Date: Sep. 28, 1981
[87] PCT Pub. No.: WO81/02096
PCT Pub. Date: Aug. 6, 1981
[51] Int. Cl.³ .......................... A61B 5/02; F61K 25/00
[52] U.S. Cl. .................... 128/685; 251/340; 251/299; 251/331
[58] Field of Search ............... 128/685, 224, 677, 276, 128/277; 251/340, 331, 299

[56] References Cited

U.S. PATENT DOCUMENTS

| 2,704,065 | 3/1955 | Clark | 128/685 |
|---|---|---|---|
| 3,030,945 | 4/1962 | Clark | 128/685 |
| 3,693,611 | 9/1972 | Ploss | 128/685 |
| 3,823,707 | 7/1974 | Hayes | 128/685 |
| 3,875,961 | 4/1975 | Gibbens | 128/685 |
| 4,037,587 | 7/1977 | Kuneda et al. | 128/685 |
| 4,050,311 | 9/1977 | Leach | 128/685 |
| 4,072,171 | 2/1978 | Nakazawa | 128/685 |
| 4,116,217 | 9/1978 | Speidel | 128/685 |
| 4,142,518 | 3/1979 | Howell | 251/342 |
| 4,146,018 | 3/1979 | Aldridge et al. | 128/685 |

FOREIGN PATENT DOCUMENTS 2284075 4/1976 France .................... 128/685

Primary Examiner—V. Millin
Assistant Examiner—Harry J. Macey
Attorney, Agent, or Firm—Holman & Stern

[57] ABSTRACT

A discharge valve for a blood pressure measuring device or the like, comprising a valve casing the interior of which is in fluid communication with an inflatable cuff and a pressure measuring device (gauge) and an air outlet leading to a flat valve seat located on the exterior of the valve casing, where the air outlet is closed off by an elastic (rubber) annular valve washer which is disposed with its central hole over a stud-shaped guide member and which has a ring-shaped control element on its outer edge, the control element being used for removing, i.e., deflecting away, the washer from the valve seat. By manual manipulation of the control element, air pressure is released with fine control from the inflated cuff.

7 Claims, 2 Drawing Figures

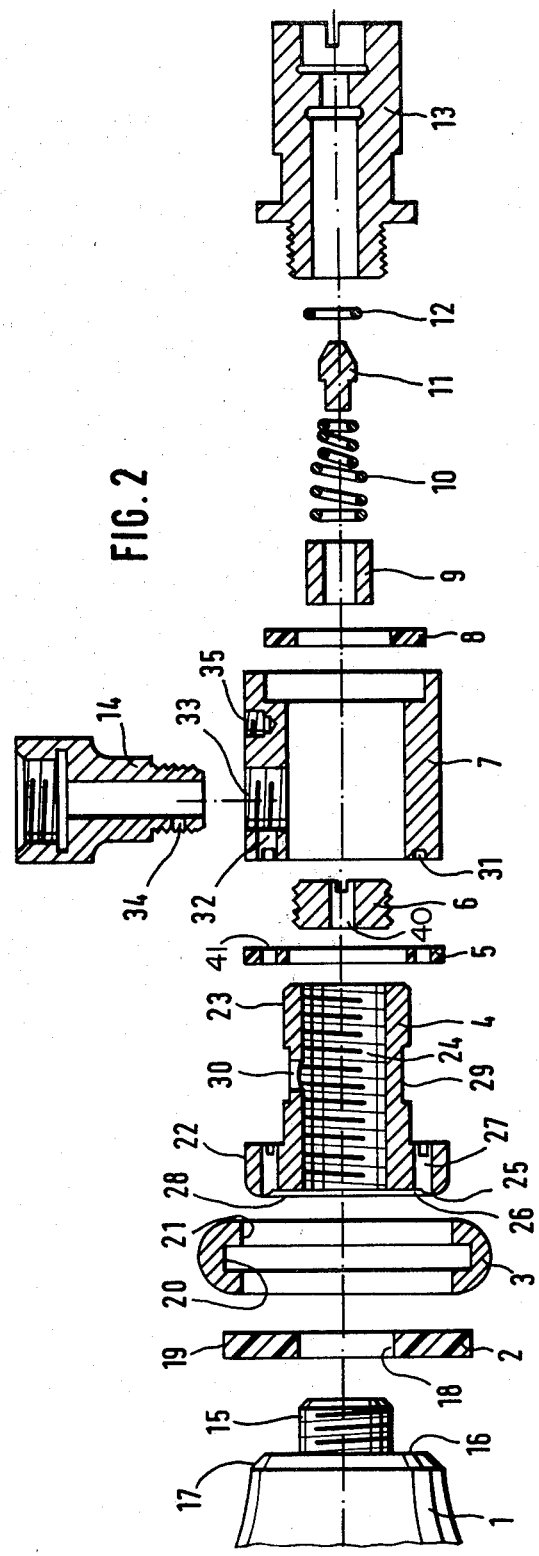

DISCHARGE VALVE FOR A BLOOD PRESSURE MEASURING DEVICE OR THE LIKE

CROSS REFERENCE TO RELATED APPLICATION

The invention of this application is disclosed in corresponding International Application No. PCT/EP-81/00010 filed January 27, 1981, the benefit of which is being claimed.

BACKGROUND OF THE INVENTION

The invention concerns a discharge valve for a blood pressure measuring device or the like wherein a valve casing the interior of which is in fluid communication with an inflatable cuff and a pressure measuring device (gauge) and an air outlet leading to a flat valve seat located on the exterior of the valve casing said air outlet is closed off by an elastic (rubber) annular valve washer which is disposed with its central hole slid over a stud-shaped guide member and which has a ring-shaped control element on its outer edge, said control element being used for removing, i.e., deflecting away, said washer from the valve seat.

One known discharge valve of this type shown in U.S. Pat. No. 4,116,217 has a pressure space located along the axis of the valve casing, to which the pressure gauge is connected in one axial direction, and in the other axial direction a rubber bulb pump is connected in the usual manner, via a check valve. The inflatable cuff is connected, for example, in ordinary manner via a rubber tube connected at the side of the valve casing. For application to blood pressure measurement for example, the pressure in the pressure space must be releasable via a discharge valve. For this purpose with the known device, connecting tubes, i.e., nipples, are connected to the pressure space at about a 45° angle to the axis, and these tubes open out into ring-shaped grooves which are coaxial to the axis of the device. These grooves are located in a ring-shaped surface piece which, in other areas, serves as a valve seat, at which location it is covered by a rubber valve washer. The valve washer is pressed against the valve seat by a valve spring, which surrounds the stud-shaped guide piece and engages the rubber washer on the side of the washer which is away from the valve seat. The valve spring is helical in shape. The inner edge of the valve washer is pressed securely against the valve casing from both sides. The outer edge is furnished with a ring-shaped control element. By manipulating this control element the valve washer can be lifted off the valve seat, with local deformation of the valve spring. This furnishes a convenient means of finely controlling the release of compressed air, which results in the intended pressure reduction in the system.

This known discharge valve having this configuration is expensive to manufacture, however, because it requires a large number of parts, some of which are difficult to fabricate, e.g. drill holes which run at an angle to the axis and are therefore hard to make, and in particular, uses a standard valve spring.

BRIEF SUMMARY OF THE INVENTION

Accordingly, the underlying problem solved by the invention is to simplify the discharge valve of the type described initially above, thereby improving it from the standpoint of manufacturing engineering, while retaining the desirable operating features. This problem is solved by the invention as characterized in the appended claims.

The discharge valve of the invention does not use a valve spring. Instead a valve washer on its side facing away from the air outlet is held against a flat, annular support surface the diameter of which is at least approximately equal to that of the circle along which the valve washer presses against the valve casing casing pressure circle on the side of said washer which faces the air outlet, and the air outlet has a smaller diameter and distance from the axis than said casing pressure circle, and the valve washer has larger diameter than said support surface.

It is seen immediately that the rubber valve washer in its circular, ring-shaped region near the axis has its flat surface lying against a flat support surface but also extending out beyond the edge of said flat support surface. This large-surface support of the inner region of the washer is aided in that on the opposite side of the washer (the side that should be regarded as the valve seat) there is pressure against the washer along a circle the diameter of which is at least approximately equal to that of the said flat support surface. Thus, by means of the large-surface support system the valve washer is held without tilting, and on the side of the washer opposite said support there is secure and continuous, concertive contact along said casing pressure circle. The circular line of pressure of the casing pressure circle has a certain finite width, of course, but this is very small. With the choice of design dimensions and configuration described, it is possible, using the control element, to slightly flex the outer part of the valve washer in the direction toward the flat support surface, thereby breaking the circular contact with the valve casing external to the air outlet on the opposite side of the washer (which contact acts to seal the air pressure), thereby producing a discharge. This discharge can be finely controlled. When the operator releases the control element, the valve washer automatically returns to its sealing position wherein it makes a circular contact with the valve casing. This return action is due to the elasticity of the washer and the way in which it is supported. Thus with this arrangement it is no longer necessary to use a valve spring, which heretofore has been regarded as an unavoidable necessity. Not only is the valve spring eliminated, but also the abutment required for the valve spring is dispensed with as well. The result is a simplification of the parts manufacturing, and also savings in materials and simplification of manufacturing procedures for the support surface and the air outlet.

A particularly expedient choice of dimensions is for the outer diameter of the support surface to be the same as or greater than that of the casing pressure circle, and for the diameter of the air outlet to be only slightly less than that of the casing pressure circle. In this way, outside of the circle there is a surface on the support-surface side of the washer which exerts a force on the washer, namely the outer edge region of the support surface. This ensures a good seal in the contact at the casing pressure circle, in particular when the valve washer is slightly thicker than the distance from the casing pressure circle (or the ring-shaped bead on the valve casing, which bead forms the circle) to the support surface. Despite this firm seal, a small excursion of the valve washer suffices to produce discharge, due to the closeness of the air outlet to the unsupported (by the support surface) region of the valve washer.

Advantageously the diameter of the valve washer is at least 1.5 times that of the support surface, preferably 2 times. This provides adequate leverage when the valve washer is deflected via the control element so that pressure reduction can be finely controlled but at the same time effectively and reliably carried out. In any event this is assured if there is a conical surface extending radially outward from the outer edge of the support surface at an angle of about 45° away from the valve washer. This provides the freedom for the valve washer to be deflected (or flexed) in the direction away from the valve seat and toward the support surface. It also provides one variant of a detent to control the maximum opening amplitude available. In this way excessive straining of the rubber washer is avoided.

It is particularly advantageous from a manufacturing engineering standpoint if the valve washer on its side facing the air outlet is held against an air outlet bushing which has a multiplicity of air outlet channels distributed in a circle around its axis, with the channels themselves running parallel to the axis, wherewith the channels open out on the end surface of said bushing facing the valve washer and interior to, i.e., at a smaller radius than, the ring-shaped bead which contacts the valve washer along the casing pressure circle and, in a ring configuration, surrounds a flat circular ring-shaped end area of said bushing while extending slightly beyond said area in the direction of the washer and the support surface. This configuration lends itself to easy manufacture with the use of automatic machine tools or high quality casting, since the parts are exclusively rotationally symmetric and-or parallel to the axis.

The air outlet bushing, at a distance from and parallel to its end plane surrounded by the ring-shaped bead, may have a ring-shaped channel which joins the air outlet channels running parallel to the axis, with said ring-shaped channel in turn being connected to a pressure channel which runs perpendicular to the axis and is connected to the pressure space, and with the connection between said ring-shaped channel and said pressure channel being through a connecting channel which runs from the side of the ring-shaped channel which is away from the valve washer and extends parallel to the axis. In this way advantageously the air outlet bushing in the region of the ring channel is reduced in one diameter step to form a cylindrical bushing shaft to which another cylindrical bushing is attached which combines with said air outlet bushing (with a seal in-between) to form said ring-shaped channel in the region of the diameter-step, whereby a connecting nipple is screwed into said cylindrical bushing, penetrating it to communicate with the pressure space, and the said connecting channel opens out through an opening in said connecting nipple. All the parts are rotationally symmetric and-or configured parallel or perpendicular to the axis, such that they can be manufactured very simply and with automated techniques, in mass production.

This easy fabrication is also true of the ring-shaped control element, which may have a semicircular cross section, with the diameter of the semicircle being at most about three times the thickness of the valve washer, wherewith the curve of the semicircle is directed outward away from the axis, and the inner side of the semicircle has a ring-shaped groove to accommodate the outer edge of the valve washer. Not only may a control element with this configuration be manufactured easily but it is desirable from the standpoint of the control action and is esthetically pleasing. The latter characteristic particularly applies to this and all other mentioned parts of the discharge valve if the material used is stainless steel.

BRIEF DESCRIPTION OF THE DRAWINGS

The invention is illustrated for purposes of example in the attached drawings, wherein FIG. 2 is an exploded view of the embodiment of FIG. 1.

DETAILED DESCRIPTION

Figure 1:
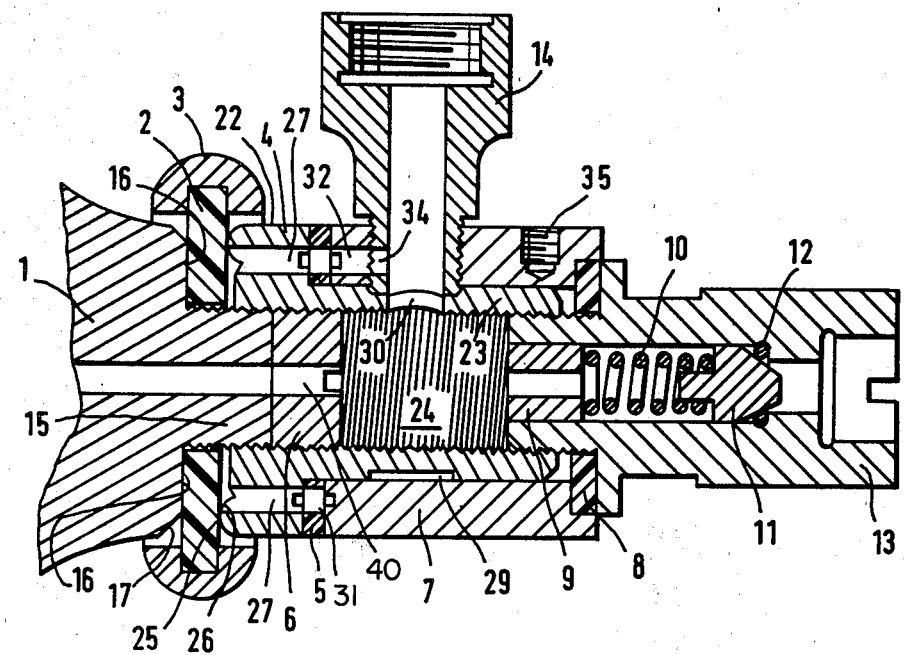
FIG. 1 shows an embodiment of the invention in cross section and in the assembled state.

The discharge valve is comprised of a pressure gauge 1, a valve washer 2, a control element in the form of an "outlet ring" 3 which surrounds the valve washer, an air outlet bushing 4 with a seal 5 and a locking (or setting) piece 6, a "scoop holder" 7 for attaching the scoop-shaped piece (not shown) which serves as a backing surface for the working of the rubber bulb pump (also not shown), a second seal 8, a bushing 9, a compression spring 10 for forcing a valve cone 11 in the direction of an O-ring 12, and a check valve body 13 working in concert with parts 10 through 12. All these parts are assembled axially as shown in FIG. 2 with the rubber bulb pump outlet being connected to the right end of check valve body 13 as viewed in the drawing. A connecting nipple 14 for an inflatable cuff (not shown) is mounted perpendicular to the axis. Specific parts will be described further below.

The pressure gauge 1 (shown in the drawings only to the extent of its end extending to the discharge valve) has a guide piece 15 in the form of a nipple extending in the axial direction, which nipple is cylindrical and threaded on the outside. Said nipple extends outward from a support surface 16 on the pressure gauge 1, with the plane of surface 16 being perpendicular to the axis. Support surface 16 is ring-shaped and flat. It does not have any indentations, openings, grooves, or countersink depressions to interfere with its supporting function. Adjoining the outer edge of support surface 16 there is a ring-shaped conical surface 17 inclined at about 45° to surface 16 in the direction away from guide piece 15. This conical surface is the link between the support surface 16 and the outer surface of the pressure gauge 1, which latter surface is configured according to (ordinary) specifications.

The assembly comprising the valve washer 2 and outlet ring (control element) 3 is mounted over the guide piece 15. Valve washer 2 is also ring-shaped. Its center hole 18 has a diameter which equals or exceeds the outer diameter of guide piece 15. The outer perimeter 19 of washer 2 is accommodated in a ring-shaped groove 20 which is formed in the inner side of outlet ring 3. This ring 3 has an approximately semicircular cross section, directed radially outward. Its inside opening 21 is cylindrical and has a ring-shaped groove 20 in it. The axial dimension of outlet ring 3 (the diameter of its outwardly directed semicircle) is about three times the thickness of valve washer 2. The diameter of the valve washer is at least 1.5 times, and preferably 2 times, that of the support surface 16.

Valve washer 2 is fabricated from a suitable elastic (rubber) material. It must be readily deformable but must return reliably and precisely to its original shape after deformation. It can be easily deflected from its rest position (shown in the drawings) by pushing on the outlet ring 3.

When the valve washer 2 and the outlet ring 3 have been assembled and mounted on the guide piece 15, the air outlet bushing 4 is screwed onto the thread of piece 15. Bushing 4 may have been previously assembled with the other parts in a manner which will be described below. The air outlet bushing has a mushroom shape and is comprised of an end flange 22 on the end near the pressure gauge, and a bushing shaft 23. The cylindrically shaped pressure space 24 is interior to bushing 4 and has an interior thread for screwing the bushing onto the exterior thread of guide piece 15. The outer diameter of end flange 22 is less than the inner diameter of inside opening 21.

End flange 22 has a ring-shaped bead 25 on its side nearest to the support surface 16 and the valve washer 2. This bead has a semicircular cross section. The apex of the semicircle forms a circle along which the ring-shaped bead 25 contacts the side of washer 2 which is nearest to the air outlet bushing 4. This circle has a diameter at least approximately equal to that of the outer diameter of support surface 16, although the diameter of the support surface may be a little greater, but not substantially greater. In this way it is ensured that the contact of washer 2 with bushing 4 along the circle at the apex of ring-shaped bead 25 can be easily broken by moving the outlet ring 3 and bending the rubber washer 2 at the transition line between the flat support surface 16 and the ring-shaped conical surface 17 whereby a circular valve seat is formed by bead 25 where it contacts valve washer 2. The air outlet proper adjoins the ring-shaped bead 25 on the inside, toward the axis. This air outlet consists of a ring-shaped channel 26 in the form of a groove into which a multiplicity of air outlet channels 27 open out, which channels 27 extend parallel to the axis in the region of the end flange 22 which lies radially outward of the outer circumference of the bushing shaft 23. At least two such air outlet channels are provided diametrically oppositely disposed with respect to each other. Because the air outlet channels 27 are interconnected by ring-shaped channel 26 into which the multiple channels 27 running parallel to the axis open out, it is not crucial where along the circular length of the apex of bead 25 the deflection of the washer 2 away from the bead 25 (by means of outlet ring 3) occurs. For uniform pressure distribution and constant flow resistance it is recommended that at least two diametrically opposite air outlet channels 27 be employed in the structure. If more than two air outlet channels 27 distributed at even distances around the ring-shaped channel 26 are used, this can only improve the performance as to uniform pressure distribution and constant flow resistance.

Adjoining the ring-shaped channel 26 on the radially inward side is a circular end surface 28 which surrounds the cylindrical opening of the pressure space 24. This surface lies in a plane which is perpendicular to the axis. The ring-shaped bead 25 extends a little beyond the plane of end surface 28 in the direction of the valve washer 2. This ensures that the valve washer on its side facing the air outlet bushing 4 is pressed against the end of bushing 4 only along the circle at the apex of bead 25.

In approximately the mid-section of bushing shaft 23 there is a flat ring-shaped groove 29 which on one side is penetrated by a radial hole 30 opening into the pressure space 24. (The purpose of this opening will be explained below.) There is a locking (or setting) piece 6 for locking or setting the air outlet bushing which is screwed onto the guide piece 15. Locking piece 6 has a diameter which matches that of guide piece 15 and has an exterior thread so that with a screwdriver or the like it can be screwed against the axial end surface of guide piece 15 and forced tight there, to serve "as" a lock nut. Of course, locking piece 6 has an axial center hole 40 through which, in the assembled state, the pressure space 24 communicates with the interior of the pressure gauge 1.

A seal 5 is slid over the outside of the air outlet bushing 4, coming together with the underside of the end flange 22 and being penetrated by openings 41 which are aligned with the air outlet channels 27. Seal 5 is held in this position by the "scoop holder" 7, which is the next piece which is slid over the bushing shaft 23 of the air outlet bushing 4. The "scoop holder" has the shape of a cylindrical sleeve, with inner diameter slightly greater than the outer diameter of shaft 23 of bushing 4, and with axial length slightly greater than that of the bushing shaft 23. In the end surface of the "scoop holder" 7 nearest to the valve washer 2 there is another ring-shaped channel 31 which interconnects the air outlet channels 27 and in turn is connected through a connecting channel 32 to a radial hole 33 having an interior thread, which in turn, through radial hole 30, is in communication with the pressure space 24. The connecting nipple 14 is screwed into radial hole 33. This nipple serves to connect an inflatable cuff, via a tube, and has a hole 34 through its threads in the region of its exterally threaded end, which threaded end is designed to screw into the radial hole 33. Hole 34 runs perpendicular to the axis of the connecting nipple, parallel to the axis of the discharge valve, and is positioned so that it lines up with the connecting channel 32 when the connecting nipple 14 is completely screwed in. The pressure space 24 is thus connected with the space next to the valve washer, via the radial hole 30, the interior of the connecting nipple 14, the hole 34 in the threads, the connecting channel 32, the ring-shaped channel 31, the air outlet channels 27, and the ring-shaped channel 26. In this way the connection of the pressure space 24 with the open atmosphere is ensured when the valve washer 2 is manipulated; and thus the pressure can be reduced in this manner.

The "scoop" (not shown in the drawings), which is held between the connecting nipple 14 and the outside of the "scoop holder" 7, additionally may be attached to holder 7 by a screw which, with the "scoop" in between, is screwed into a threaded hole 35 extending radially into the wall of holder 7 at a location next to the radial hole 33 on a common line running through the centers of holes 35 and 33 parallel to the axis of the valve (said line being an imaginary line on the surface of holder 7).

The assembly of the discharge valve is completed by mounting parts 8 through 13 on the remaining open end of "scoop holder" 7 as shown and securing the threaded end of check valve body 13 by screwing them into the interior thread of the air outlet bushing 4. The operation of the check valve thus installed is self-evident and need not be described in detail. When the rubber bulb pump (not shown) is squeezed, the valve 11, by moving away from the O-ring 12, enables the pressure in pressure space 24 to be increased and at the same time communicated to the pressure gauge 1 and (via connecting nipple 14) to the inflatable cuff.

The "scoop holder" 7 has, for a total length of about 2 cm, a diameter of about 1.5 cm. In this way an ergonomically favorable support or holding by the operator's thumb and forefinger on the outer circumference of "scoop holder" 7 is set up, through the rubber bulb pump (which is connected to check valve 13) and the "scoop" which is located adjoining said pump. This feature applies also both for mere holding of outlet ring 3 and for manipulation of outlet ring 3, which ring is also ergonomically favorably positioned. From a manufacturing standpoint, the compact and rugged construction is of particular advantage since only a small number of parts are used, all of which can be economically produced on automatic machinery.

I claim:

1. In a discharge valve for a blood pressure measuring device or the like, including a valve casing having a central bore therethrough which is in fluid communication with an inflatable cuff, a pressure measuring device and an air outlet, with said air outlet leading to an outlet valve seat located on the exterior of the valve casing, the improvement wherein said valve seat is circular, comprising an elastic annular valve washer concentrically disposed with respect to said circular valve seat and engaging said seat on one side thereof, a stud-shaped guide member on which said valve washer is mounted, a ring-shaped control element mounted on the outer edge of said valve washer for deflecting said washer from the valve seat, a flat, annular support surface engaging the other side of said valve washer having an outer diameter at least approximately equal to that of said circular valve seat along which the valve washer presses against the valve casing on the side of said washer which faces the air outlet, a conical ring-shaped surface extending radially outward from the outer diameter of said support surface at an angle of about 45° away from the valve washer, the air outlet having a smaller diameter than said circular valve seat, and the valve washer having a larger outer diameter than said support surface.

2. Discharge valve according to claim 1 wherein the diameter of the support surface is equal to that of the circular valve seat, and the (diameter of the air outlet) is only slightly less than that of the circular valve seat.

3. Discharge valve according to claim 1 wherein the diameter of the valve washer is at least 1.5 times times that of said support surface (16).

4. Discharge valve according to claim 1 wherein said valve casing comprises an air outlet bushing, a plurality of air outlet channels in circumferential spaced relationship around the central axis of said bushing, with the channels themselves running parallel to said axis, said channels opening out on the end surface of said bushing facing the valve washer, a ring-shaped bead on said end surface which contacts the valve washer along said circular valve seat, a flat ring-shaped channel on said end surface of said bushing having an outer diameter large enough to communicate with said outlet channels and communicating with said central bore of the valve casing at its inner diameter.

5. Discharge valve according to claim 4 wherein said air outlet bushing, at a distance from and parallel to said end surface facing the valve washer has a second ring-shaped channel communicating with said air outlet channels which runs from the side of the ring-shaped channel away from the valve washer and extends parallel to said central axis of the bushing, and a pressure channel extending perpendicular to said central axis and communicating with said central bore and said connecting channel.

6. Discharge valve according to claim 5 wherein said air outlet bushing has a reduced diameter section to form a cylindrical bushing shaft and further comprising a cylindrical bushing in surrounding engagement with said bushing shaft which combines with said air outlet bushing to form said second ring shaped channel, in the region of the diameter reduction, an annular seal member interposed between the end of said cylindrical bushing and said air outlet bushing, a connecting nipple threadedly connected into said pressure channel, the latter being in said cylindrical bushing, penetrating it and said air outlet bushing to communicate with said central core, and said connecting channel extends through said connecting nipple.

7. Discharge valve according to claim 1 wherein said ring-shaped control element has a semicircular cross section, with the diameter of the semicircle being about three times the thickness of said valve washer, the curved surface of the semicircle being directed outwardly with respect to said valve washer, and a ring-shaped groove in the inner surface of said control element operatively engaging the outer edge of the valve washer.

* * * * *